US010973430B2

(12) United States Patent
Morshed et al.

(10) Patent No.: US 10,973,430 B2
(45) Date of Patent: Apr. 13, 2021

(54) FULLY RECONFIGURABLE MODULAR BODY-WORN SENSORS

(71) Applicant: The University of Memphis, Memphis, TN (US)

(72) Inventors: Bashir I. Morshed, Germantown, TN (US); Ruhi Mahajan, Memphis, TN (US)

(*) Notice: Subject to any disclaimer, the term of this patent is extended or adjusted under 35 U.S.C. 154(b) by 758 days.

(21) Appl. No.: 14/938,954

(22) Filed: Nov. 12, 2015

(65) Prior Publication Data
US 2016/0128596 A1  May 12, 2016

Related U.S. Application Data

(60) Provisional application No. 62/078,822, filed on Nov. 12, 2014.

(51) Int. Cl.
*A61B 5/04* (2006.01)
*A61B 5/0476* (2006.01)
*A61B 5/00* (2006.01)

(52) U.S. Cl.
CPC .......... *A61B 5/0476* (2013.01); *A61B 5/0024* (2013.01); *A61B 5/04004* (2013.01); *A61B 5/725* (2013.01); *A61B 5/002* (2013.01); *A61B 5/0002* (2013.01); *A61B 5/0006* (2013.01); *A61B 5/7225* (2013.01)

(58) Field of Classification Search
CPC . A61B 5/0476; A61B 5/04004; A61B 5/0024; A61B 5/725; A61B 5/7225; A61B 5/0002; A61B 5/0006; A61B 5/002
See application file for complete search history.

(56) References Cited

U.S. PATENT DOCUMENTS

| | | | | |
|---|---|---|---|---|
| 5,217,010 A | * | 6/1993 | Tsitlik | A61B 5/0424 607/9 |
| 5,392,784 A | * | 2/1995 | Gudaitis | A61B 5/0428 128/902 |
| 9,853,611 B2 | * | 12/2017 | Chang | H03F 3/45183 |
| 2005/0203366 A1 | * | 9/2005 | Donoghue | A61B 5/04002 600/378 |
| 2008/0159365 A1 | * | 7/2008 | Dubocanin | A61B 5/04004 375/219 |
| 2010/0106041 A1 | * | 4/2010 | Ghovanloo | A61B 5/0006 600/544 |

(Continued)

*Primary Examiner* — Navin Natnithithadha
*Assistant Examiner* — Andrey Shostak
(74) *Attorney, Agent, or Firm* — Wayne Edward Ramage; Baker Donelson

(57) ABSTRACT

A system is disclosed including: one or more electroencephalography (EEG) sensor nodes in a fully reconfigurable sensor network configured to detect electrical signals indicating activity of a brain of a subject and to transmit signal information relating to the detected electrical signals, each EEG sensor node embodying an analog front end (AFE) circuit, and a centralized command control node (CCN) in the sensor network in communication with the one or more EEG sensor nodes and configured to receive the transmitted signal information from the one or more EEG sensor nodes and to perform a processing technique on the received information resulting in processed signal data, wherein the one or more EEG sensor nodes are configured to detect the electrical signals without a driven right leg (DRL) circuit in the sensor network.

14 Claims, 12 Drawing Sheets

(56) References Cited

U.S. PATENT DOCUMENTS

| | | | | |
|---|---|---|---|---|
| 2011/0251469 A1* | 10/2011 | Varadan | ............... | A61B 5/113 |
| | | | | 600/301 |
| 2012/0095361 A1* | 4/2012 | Xu | ............... | A61B 5/04004 |
| | | | | 600/547 |
| 2012/0242501 A1* | 9/2012 | Tran | ............... | A61B 5/0024 |
| | | | | 340/870.02 |
| 2013/0231947 A1* | 9/2013 | Shusterman | ............... | G06F 19/3418 |
| | | | | 705/2 |
| 2013/0338518 A1* | 12/2013 | Zoica | ............... | A61B 5/7225 |
| | | | | 600/516 |
| 2014/0051946 A1* | 2/2014 | Arne | ............... | A61B 5/0022 |
| | | | | 600/301 |
| 2014/0107501 A1* | 4/2014 | Komanduri | ............... | A61B 5/0205 |
| | | | | 600/484 |
| 2014/0194944 A1* | 7/2014 | Romanelli | ............... | A61B 5/0031 |
| | | | | 607/45 |
| 2014/0371611 A1* | 12/2014 | Kim | ............... | A61B 5/0416 |
| | | | | 600/509 |
| 2016/0113540 A1* | 4/2016 | Chi | ............... | A61B 5/6843 |
| | | | | 600/509 |

\* cited by examiner

FULLY RECONFIGURABLE MODULAR BODY-WORN SENSORS

TECHNICAL FIELD

The present disclosure relates generally to body-worn sensors and, more particularly, to a sensor-level modular and reconfigurable electroencephalography (EEG) system.

BACKGROUND

In general, electroencephalography (EEG) refers to the non-invasive recording of human brain cortical electrical activities, typically recorded by placing EEG sensors at the scalp. EEG sensors reliably measure voltage fluctuations that result from ionic current flows within the neurons of the brain. These voltage fluctuations can be classified according to their spectral content. In this regard, as specific brain lobes are responsible for certain activities, cognitive loads and engagement can be classified from spatially collected EEG data. For example, the frontal lobe is more responsible for problem solving, mental flexibility, judgment and creativity. EEG signals are typically classified as delta (0.1-3.5 Hz), theta (4-7.5 Hz), alpha (8-13 Hz), beta (14-30 Hz), and gamma (>30 Hz) rhythms. EEG rhythms can be analyzed to assess the mental states and neuronal activities of subjects and can be medically beneficial for neurological disorder patients.

In addition to EEG systems, several other physiological sensor systems can be body-worn to collect multimodal data from the subject that can individually or collectively be processed to interpret abnormalities, disorders, and the like. Currently, these body-worn sensor systems are developed independently, and communication is established at the system-level among various data collecting devices. To this point, in traditional architectures, neurological and physiological data collection and processing devices are disjointed and overly customized for specific signals. Because each system is highly optimized for a specific application, they do not allow fully reconfigurable architecture. This becomes especially problematic for measuring bioelectric signals, as in EEG and electrocardiography (ECG/EKG), which require a driven right leg (DRL) circuit, thereby prohibiting modularization of a physiological sensor system and the ability to dynamically reconfigure the same.

A DRL circuit is an electric circuit that is often added to biological signal amplifiers to reduce common-mode interference. This interference can obscure the biological signals, making them difficult to measure. Such circuitry is typically required in EEG systems and provides a feedback path to the body by combining signals from all channels, a concept originated from early experiments of bio-potentials, such as ECG. The prime rationales of DRL are to eliminate (a) potentially dangerous current flow through the ground loop, (b) large voltage build up on a patient across a poorly connected electrode, and (c) interference noise by actively canceling the interference.

However, non-optimized design of a DRL circuit can increase differential mode noise if not properly matched, which poses a severe design barrier for modular and fully-reconfigurable plug-and-play sensor-based EEG systems. As a result, the requisite involvement of DRL circuitry presents significant challenges to performing transformative personalized healthcare, ubiquitous monitoring, and pervasive assistive technologies, as well as understanding of brain functionalities in natural environments using non-invasive methods while the individual is interacting with its surroundings. Accordingly, in order to effectively collect neurophysiological information in view of the above considerations, sensor systems which are fully reconfigurable, modular, and intelligent are needed.

SUMMARY

According to embodiments of the present disclosure, a system is disclosed, including: one or more electroencephalography (EEG) sensor nodes in a fully reconfigurable sensor network to detect electrical signals indicating activity of a brain of a subject and to transmit signal information relating to the detected electrical signals, each EEG sensor node embodying an analog front end (AFE) circuit; and a centralized command control node (CCN) in the sensor network in communication with the one or more EEG sensor nodes and configured to receive the transmitted signal information from the one or more EEG sensor nodes and to perform a processing technique on the received information resulting in processed signal data, wherein the one or more EEG sensor nodes are configured to detect the electrical signals without a driven right leg (DRL) circuit in the sensor network.

One or more other sensor nodes, other than EEG sensor nodes, may be connected in the sensor network, in communication with the CCN, and configured to detect other signals and to transmit information relating to the detected other signals to the CCN. The one or more EEG sensor nodes may be in communication with the one or more other sensor nodes. The one or more other sensor nodes may be further configured to be worn by the subject. The other signals may be associated with physiological data of the subject. Also, the other signals may be associated with location data of the subject.

The one or more EEG sensor nodes may be configured to locally perform a processing technique on the detected electrical signals resulting in processed signal data and to transmit the processed signal data to the CCN.

The AFE circuit may include, in order, a first amplifier, a notch filter, a low-pass filter, a high-pass filter, and a second amplifier.

The one or more EEG sensor nodes and/or the one or more other sensor nodes may be wirelessly in communication with the CCN.

The sensor network may be configured according to an inter-integrated circuit (I2C) topology.

The CCN may be further configured to control an aspect of the sensor network and to control an aspect of the one or more EEG sensor nodes. Also, the CCN may be further configured to dynamically control the one or more EEG sensor nodes so as to adapt to a changing condition associated with the subject.

A wireless bridge node (WBN) may provide wireless extension of the sensor network to one or more wireless sensor nodes.

Sensor nodes of any type can be added to or removed from the sensor network (e.g., in fully reconfigurable fashion as plug-and-play modules during deployment).

According to embodiments of the present disclosure, a method is disclosed, including: detecting, by one or more electroencephalography (EEG) sensor nodes in a fully reconfigurable sensor network, electrical signals indicating activity of a brain of a subject, each EEG sensor node embodying an analog front end (AFE) circuit; and transmitting, from the one or more EEG sensor nodes, signal information relating to the detected electrical signals to a centralized command control node (CCN) in the sensor network configured to perform a processing technique on the transmitted information, wherein the one or more EEG sensor nodes detect the electrical signals without a driven right leg (DRL) circuit in the sensor network.

One or more other sensor nodes, other than EEG sensor nodes, may be connected in the sensor network, in communication with the one or more EEG sensor nodes, and configured to detect other signals and to transmit information relating to the detected other signals to the CCN.

The one or more EEG sensor nodes may locally perform a processing technique on the detected electrical signals resulting in processed signal data and transmit the processed signal data to the CCN.

According to embodiments of the present disclosure, a method is disclosed, including: receiving, at a centralized command control node (CCN) in a fully reconfigurable sensor network, signal information relating to electrical signals indicating activity of a brain of a subject detected by one or more electroencephalography (EEG) sensor nodes in the sensor network, each EEG sensor node embodying an analog front end (AFE) circuit; and performing, by the CCN, a processing technique on the received information resulting in processed signal data, wherein the one or more EEG sensor nodes detect the electrical signals without a driven right leg (DRL) circuit in the sensor network.

One or more other sensor nodes, other than EEG sensor nodes, may be connected in the sensor network, in communication with the CCN, and configured to detect other signals and to transmit information relating to the detected other signals to the CCN.

The CCN may control an aspect of the sensor network and an aspect of the one or more EEG sensor nodes.

BRIEF DESCRIPTION OF THE DRAWINGS

The foregoing and other objects, features, aspects and advantages of the embodiments disclosed herein will become more apparent from the following detailed description when taken in conjunction with the following accompanying drawings.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

To facilitate an understanding of the present invention, a number of terms and phrases are defined below. As used herein, the singular forms "a", "an", and "the" include plural forms unless the context clearly dictates otherwise. Thus, for example, reference to "a signal" includes reference to more than one signal. Unless specifically stated, or obvious from context, as used herein, the term "or" is understood to be inclusive.

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes related art embodiments.

As used herein, the term "subject" is meant to refer to an animal, preferably a mammal including a non-primate (e.g., a cow, pig, horse, cat, dog, rat, mouse, etc.) and a primate (e.g., a monkey, a human, etc.), and more preferably a human. In a preferred embodiment, the subject is a human.

According to embodiments of the present disclosure, a sensor-level modular and fully reconfigurable EEG system has been disclosed that is capable of being paired with other body-worn sensor systems and allows for LEGO® like plug-and-play connectivity of multimodal sensors on the body. This can be achieved by eliminating DRL, circuitry from the conventional EEG (as well as ECG) systems. Instead, the AFE circuit design disclosed herein may be independently utilized for each channel. Consequentially, the number of EEG channels (i.e., sensor nodes) can be one or many, independent of the design, and can be customized at the time of deployment. Subsequently, the EEG system as disclosed herein can incorporate any type of body-worn sensors within the sensor network (via a wired or a wireless connection). Additionally, the EEG system may implement distributed intelligence among the sensor nodes by using "smart" sensor nodes equipped to perform computations on the locally acquired sensor data.

Figure 1:
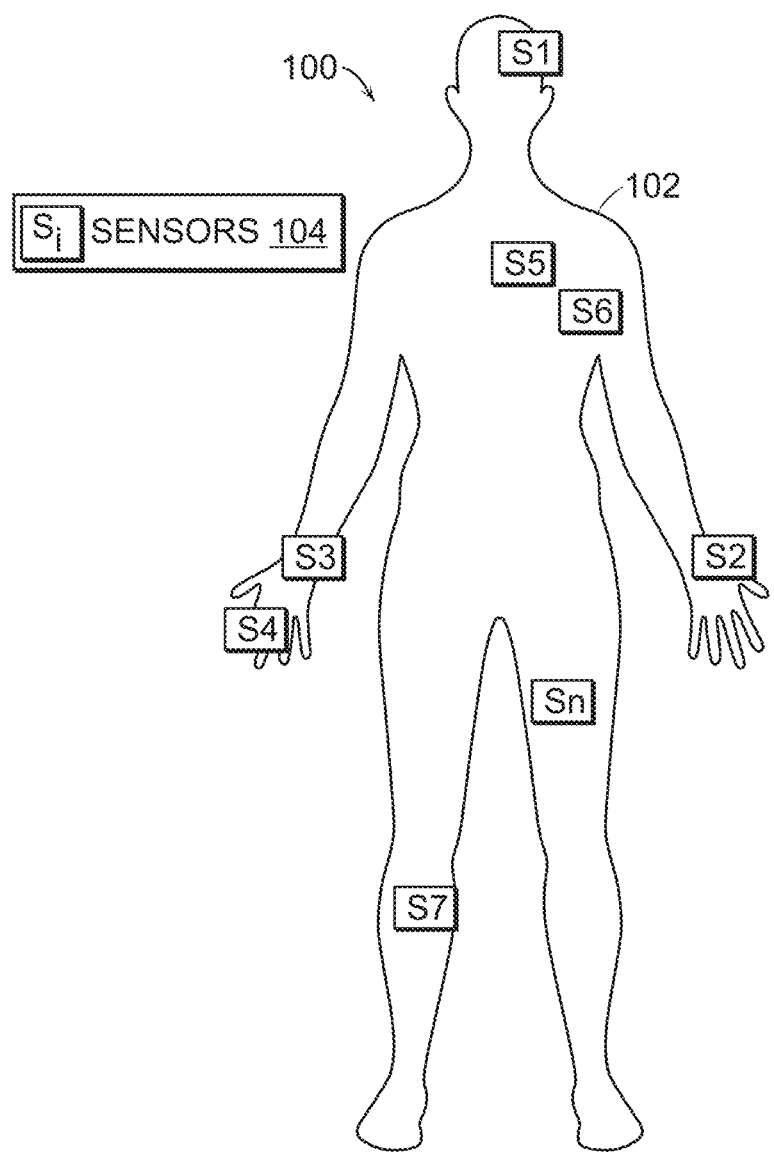
FIG. 1 illustrates an example biosensor system.

FIG. 1 illustrates an example biosensor system. As shown in FIG. 1, the sensor system 100 may include any number of sensors 104 (e.g., sensors S1 to Sn) that may be worn by, or implanted into, a subject 102. During operation, sensors 104 measure any number of different biosignals from subject 102. In other words, sensors 104 may convert measured biological responses from subject 102 into values represented as an electrical property (e.g., a current, voltage, resistance, capacitance, inductance, impedance, etc.). For example, the brain activity of subject 102 may be measured by one of sensors 104 (e.g., S1) using an EEG sensor, i.e., an electrode placed on the scalp of the subject 102, that measures voltage fluctuations resulting from ionic current flows within the neurons of the brain. Thus, a change in the voltage and electrical response of the EEG sensor indicates a corresponding change in the brain activity of subject 102.

Sensors 104 may measure one or more types of biosignals from subject 102. For example, sensors 104 may take any or all of the following biological and/or physiological measurements from subject 102: a temperature measurement, a pulse measurement, a galvanic skin response measurement, a pulse oximetry measurement, an electrocardiography measurement, an electroencephalography measurement, combinations thereof, or the like. Notably, it may be possible to pair sensors which are not configured to perform biological or physiological measurements, such as a GPS sensor, an air temperature sensor, a noise sensor, and so forth, with the biosensors 104.

Figure 2:
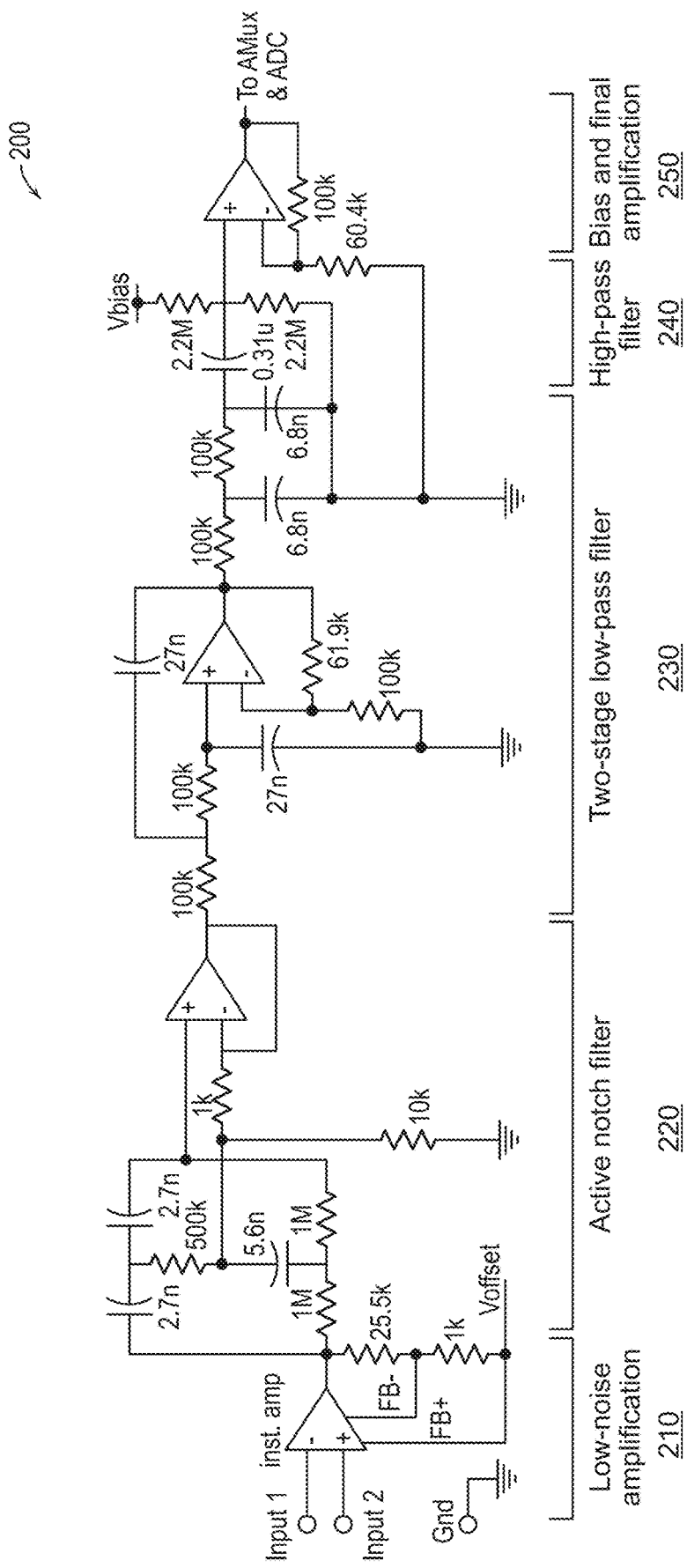
FIG. 2 illustrates an example analog front end design of a single EEG channel which eliminates DRL circuitry according to embodiments of the present disclosure.

FIG. 2 illustrates an example AFE design of a single EEG channel which eliminates DRL circuitry according to embodiments of the present disclosure. As shown in FIG. 2, the EEG sensor node circuit 200 may include various circuit segments including, in order, low-noise amplification segment 210, active notch filter segment 220, two-stage low-pass filter segment 230, high-pass filter 240, and bias and final amplification segment 250. Notably, the illustrative configuration of the circuit 200 is depicted merely as a single working embodiment and for demonstration purposes only and thus, should not be understood as limiting the circuit 200 to only the configuration shown in FIG. 2. Rather, the EEG sensor node circuit 200 may be configured in any manner as would be understood by one of ordinary skill in the art to embody an AFE circuit suitable for performing EEG measurements. That is, the EEG sensor node circuit 200 may be designed according to a variety of configurations.

As is understood in the art, AFE circuitry refers to a set of analog signal conditioning circuitry that uses operational amplifiers, filters, and/or application-specific integrated circuits to provide a configurable and flexible electronics functional block, e.g., for sensors and other circuits. AFE hardware modules can be used to interface sensors of many kinds to digital systems, thereby providing hardware modularity.

With respect to the present disclosure, as shown in FIG. 2, the AFE may be designed in such a way that the EEG system can access comparable EEG signal data from the subject 102 without any DRL circuit in the system. To this end, a notch filter (e.g., active notch filter 220) may be added after a differential amplifier with limited amplification (e.g., low-noise amplification 210), followed by an active bandpass filter (e.g., two-stage low pass filter 230), a level restorer (DC offset) circuit (e.g., high-pass filter 240). Then, the filtered signal may be finally amplified (e.g., bias and final amplification 250). Generally, the AFE circuit may include, in order, a first amplifier, a plurality of filters, and a second amplifier. As such, the elimination of DRL circuit allows for greater modularization and configurability of an EEG system, particularly at the sensor-level, allowing for any number of EEG sensors within the sensor network at deployment.

FIGS. 3A-3D demonstrate that the AFE circuit design illustrated in FIG. 2, which eliminates DRL circuitry, maintains signal quality comparable to that of a conventional EEG system configured with DRL circuitry. Generally, noise analysis reveals only minor signal degradation (e.g., up to 2 dB at 60 Hz) when using an AFE for a single-channel EEG sensor without DRL circuitry.

Figure 3A:
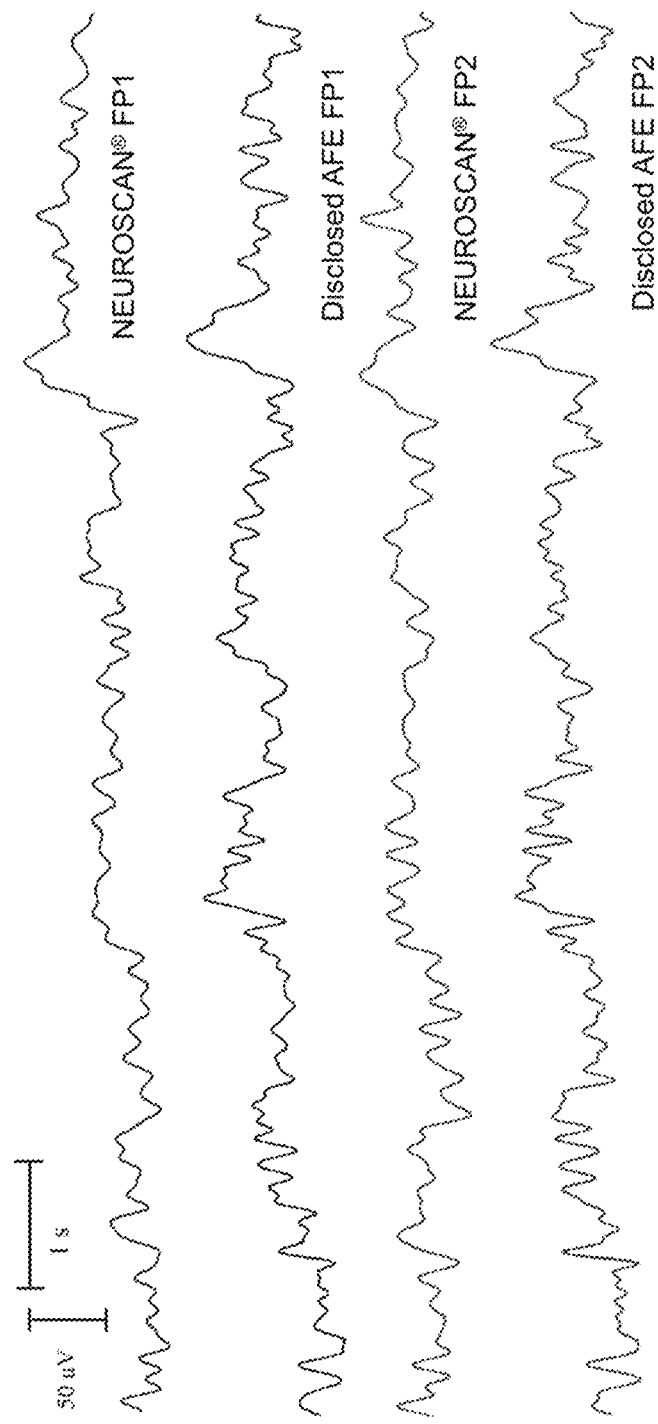
FIG. 3A illustrates an example temporal domain comparison of an EEG system that eliminates DRL circuitry according to embodiments of the present disclosure (i.e., "Disclosed AFE") and a conventional EEG system configured with DRL circuitry (i.e., "NEUROSCAN®") from the FP1 and FP2 locations.

In this regard, FIG. 3A illustrates an example temporal domain comparison of an EEG system that eliminates DRL circuitry according to embodiments of the present disclosure and a conventional EEG system configured with DRL circuitry. As shown in FIG. 3A, EEG signal quality at the FP1 and FP2 positions (as defined by the International 10-20 system for EEG) is highly similar for a DRL-based EEG system (i.e., "NEUROSCAN®") and an AFE- and non-DRL-based EEG system over time.

Figure 3B:
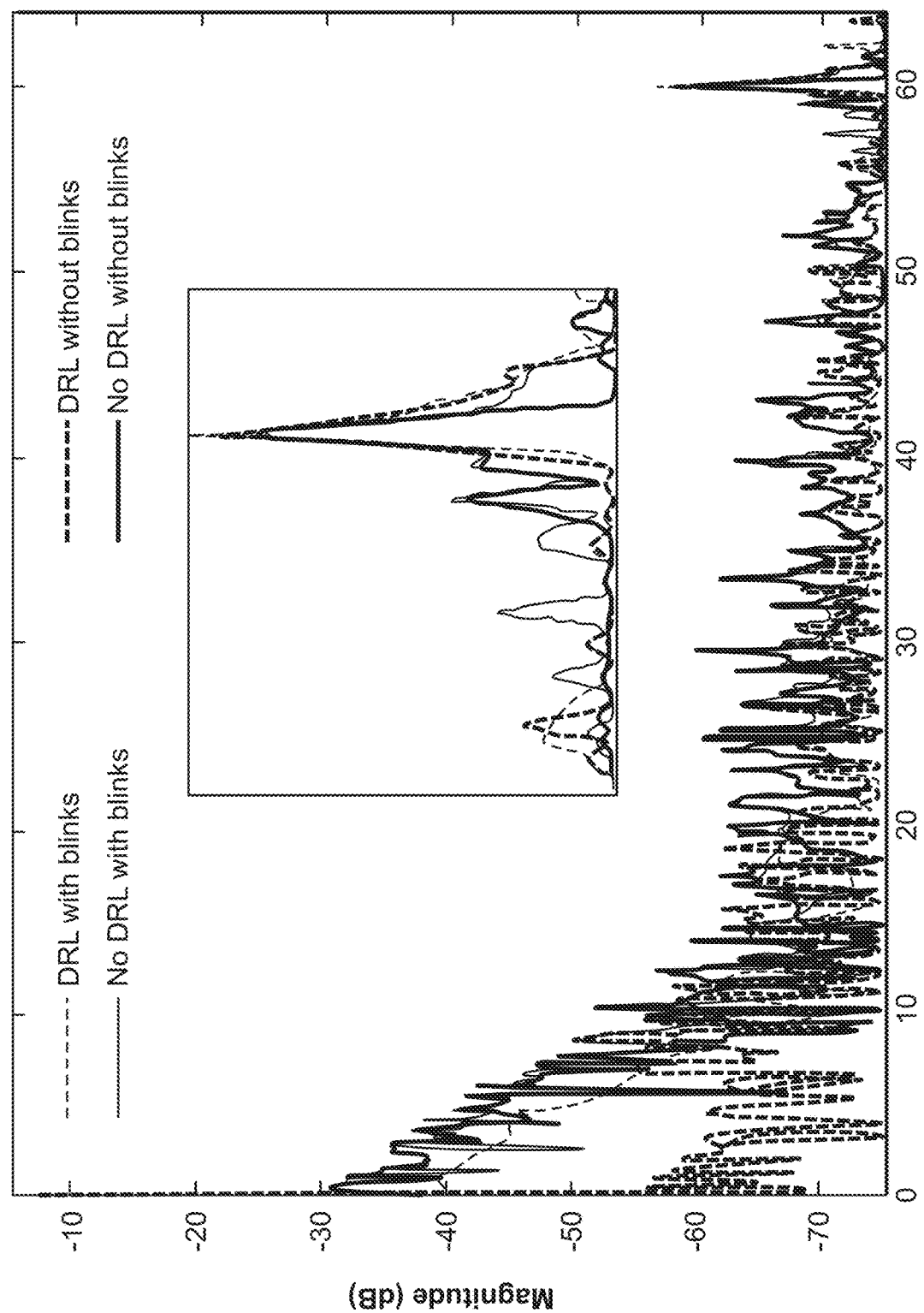
FIG. 3B illustrates an example Fast Fourier Transform (FFT) comparison of the EEG system that eliminates DRL circuitry according to embodiments of the present disclosure and the conventional EEG system configured with DRL circuitry for EEG data with and without blink artifacts.

FIG. 3B illustrates an example Fast Fourier Transform (FFT) comparison of the EEG system that eliminates DRL circuitry according to embodiments of the present disclosure and the conventional EEG system configured with DRL circuitry for EEG data with and without blink artifacts. Artifacts refer to signals detected by EEG sensors originating from a non-cerebral source. For instance, eye-induced artifacts, such as eye blinks, eye movements and extra-ocular muscle activity, commonly contaminate EEG data, potentially creating large amplitudes relative to the size of amplitudes of the cortical signals of interest. As shown in FIG. 3B, the magnitude for DRL-based and AFE-based (i.e., without DRL circuitry) EEG systems is comparable over a frequency range of 0-60 Hz, even when accounting for blink artifacts.

Figure 3C:
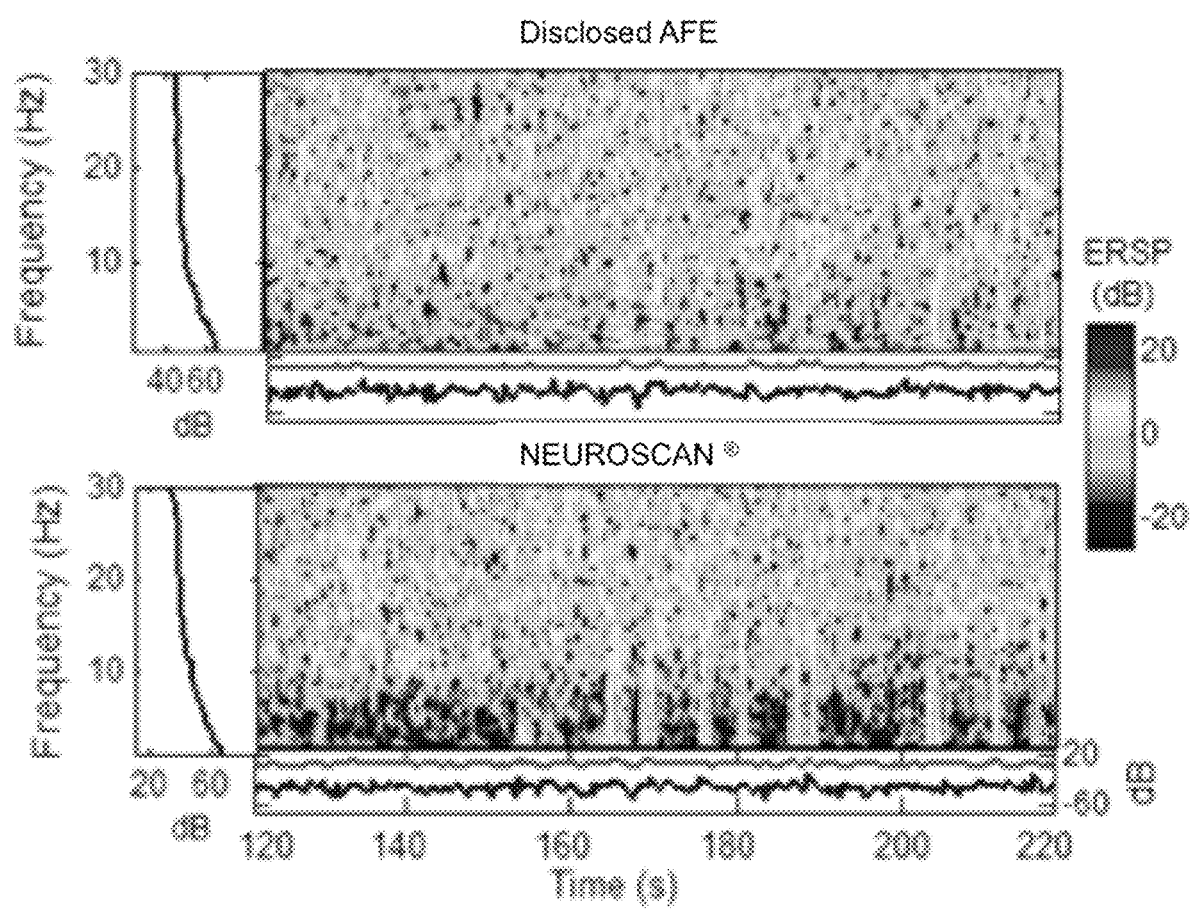
FIG. 3C illustrates an example time-frequency spectrogram comparison of a subject's EEG data from the FP1 location in the EEG system that eliminates DRL circuitry according to embodiments of the present disclosure (i.e., "Disclosed AFE") and in the conventional EEG system configured with DRL circuitry (i.e., "NEUROSCAN®").

FIG. 3C illustrates an example time-frequency spectrogram comparison of a subject's EEG data in the EEG system that eliminates DRL circuitry according to embodiments of the present disclosure and in the conventional EEG system configured with DRL circuitry. As shown in FIG. 3C, spectrogram data (i.e., time-frequency) at the FP1 position is highly similar for a DRL-based EEG system (i.e., "NEUROSCAN®") and an AFE- and non-DRL-based EEG system over time.

Figure 3D:
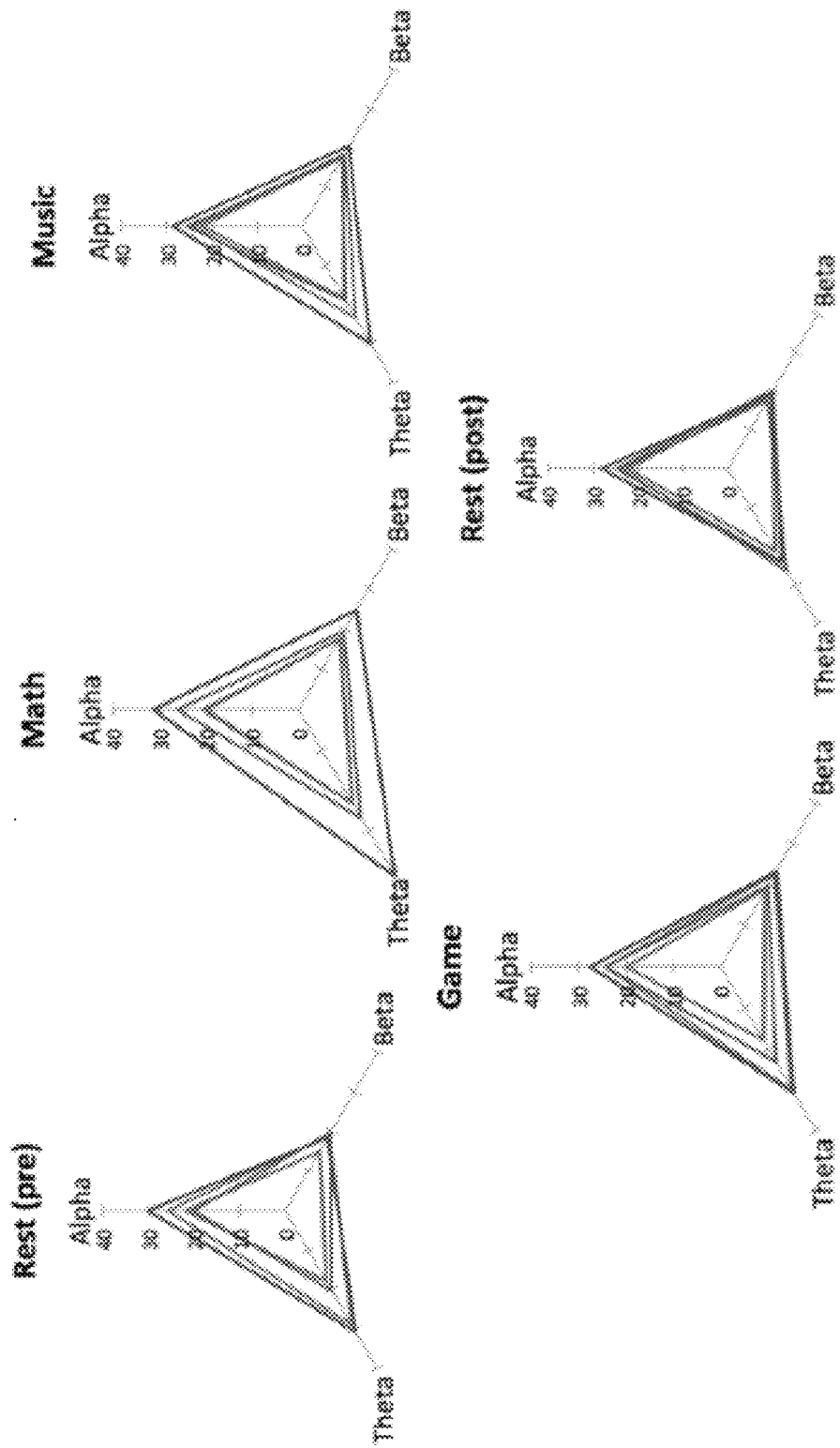
FIG. 3D illustrates an example identification of variation in different EEG rhythms for various cognitive tasks with EEG data from the EEG system that eliminates DRL circuitry according to embodiments of the present disclosure for four subjects (each line indicating a different subject) performing various activities.

FIG. 3D illustrates identification of variation in different EEG rhythms for various cognitive tasks with EEG data from the EEG system that eliminates DRL circuitry according to embodiments of the present disclosure for four subjects (each indicated with a different color) performing various activities. A cognitive load index (CLI) can be computed to monitor brain engagement activity in real-life settings. Specifically, in order to analyze attention levels for different real-life tasks, EEG rhythms (e.g., alpha, beta, and theta signals) can be extracted and the CLI can be computed. The results may show variations in the PSD of the EEG rhythms with respect to expected cognitive loads in the tasks of interest.

As shown in FIG. 3D, the signal power for different rhythms for four subjects performing five different tasks (e.g., rest, math, music, game, rest) is mapped based on signal data acquired by an AFE-based (i.e., without DRL circuitry) EEG system at the FP1 position. The analysis shown in FIG. 3D is successful in that the signal power for different rhythms of the subjects varies in accordance to the task and cognitive loads.

Figure 4:
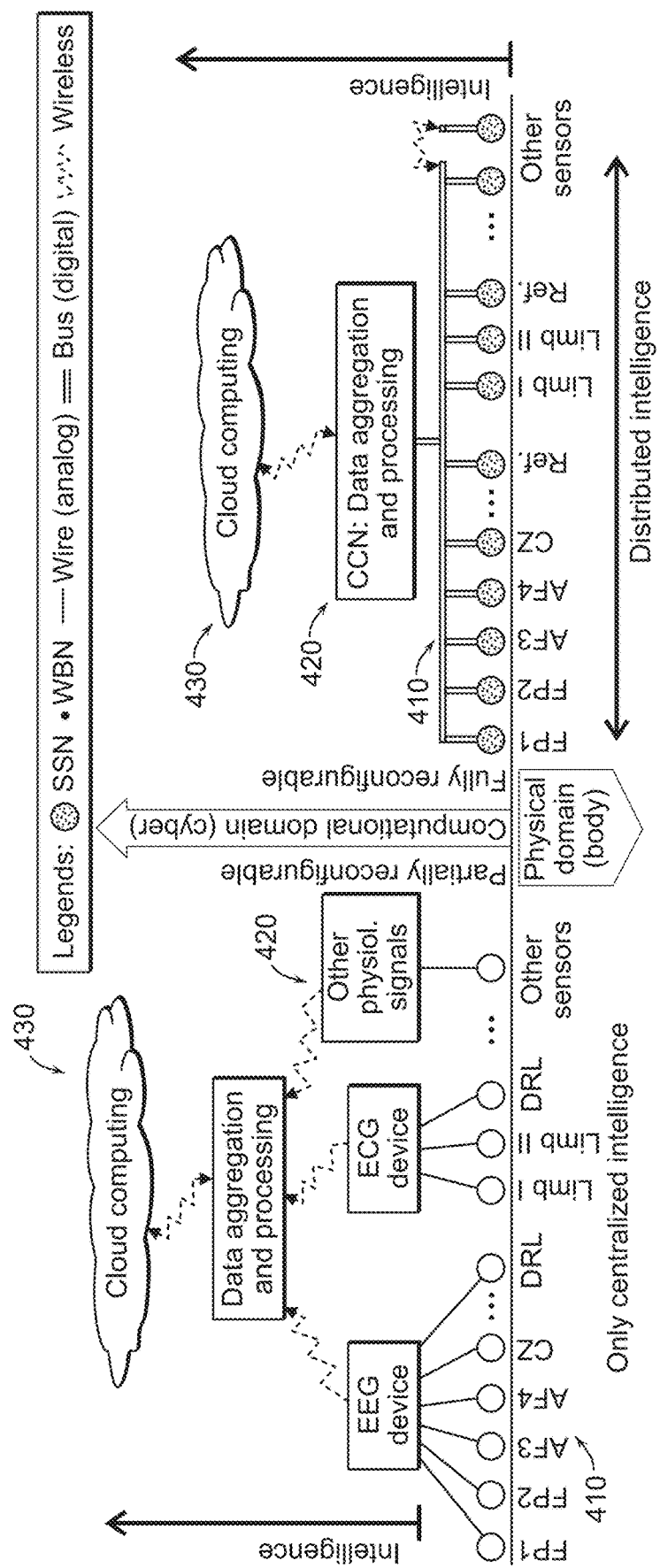
FIG. 4 illustrates an example schematic comparison of the high-level connectivity between a conventional EEG system configured with DRL circuitry and other body-worn sensor systems and the high-level connectivity between the centralized command control node and the EEG smart sensor nodes according to embodiments of the present disclosure.

FIG. 4 illustrates an example schematic comparison of the high-level connectivity between a conventional EEG system configured with DRL circuitry and other body-worn sensor systems (at left), and the high-level connectivity between a centralized command control node (CCN) and the EEG sensor nodes according to embodiments of the present disclosure (at right). As shown in FIG. 4, at left, a sensor network including a conventional DRL-based EEG system combined with other biometric sensor systems and connected to a data collection device is depicted. Meanwhile, at right, a sensor network including the presently disclosed AFE-based (i.e., without DRL circuitry) EEG system connected to other sensor systems and a data collection device (e.g., "CCN") is depicted for the sake of comparison. The illustration depicts the high-level connectivity of each system at their respective sensor-level 410, data collection-level 420, and server- or cloud-level 430.

With respect to the presently disclosed AFE-based EEG system according to embodiments of the present disclosure, a modular and reconfigurable architecture may be realized using a set of EEG sensor nodes that are "smart" sensor nodes (SSN), which replace the traditional "non-intelligent" sensors (e.g., as shown at the sensor-level 410) that merely collect and transmit data. That is, the EEG sensor nodes may be capable of performing processing techniques, e.g., data analysis, on the locally sensed data. As a result, EEG SSNs with distributed intelligence can locally process sensed data to identify noteworthy features and events of interest in real-time and transmit the processed signal data to the centralized CCN, thereby significantly reducing data payload of the network. Thus, the processing intelligence can start from the sensor-level 410 and up, rather than from the data collection-level 420 and up (e.g., "centralized intelligence"), as in the conventional DRL-based system shown in FIG. 4.

Similarly, the AFE-based EEG system may replace the traditional "non-reconfigurable" specific data collection devices with a generic and universal CCN, which can accommodate any type of sensor (e.g., as shown at the data collection-level 420). In addition to data aggregation and network arbitration, the CCN may control aspect(s) of the sensor network and aspect(s) of the EEG sensor nodes, such as dynamically controlling the EEG sensor nodes so as to adapt to a changing condition associated with the subject. That is, the CCN may synchronize and reconfigure the sensor network and the EEG SSNs as the subject adapts to dynamic conditions.

The CCN at the data collection-level 420 may receive transmitted signal information from the sensor nodes (EEG sensors or non-EEG sensors). The received signal information may include the raw data signals, as collected by the sensors, processed signal data (e.g., signal data subjected to processing by a smart sensor), or both. The CCN may subsequently take a variety of actions with respect to the received signal information, such as, for example, storing the information, processing the information (e.g., performing data analysis), forwarding the information (whether processed or not) to a remote location for further storage/processing (e.g., cloud-level 430), controlling the sensor nodes based on the received information (e.g., disabling/enabling particular nodes, etc.), controlling sensor network settings based on the received information, and so forth. Note that the above examples do not limit the functionality of the CCN but rather are intended for demonstration purposes only.

Due to the elimination of DRL circuitry, as well as the involvement of a universal CCN for collecting the sensed data, one or more other sensor nodes may be connected in the sensor network (as shown in FIG. 4). That is, in addition to EEG, the sensor network can incorporate SSNs for sensing other biological and/or physiological activity, such as ECG, heart rate variability (HRV), breathing pattern, pulse oximetry, posture/orientation, body temperature, and so forth. Furthermore, any type of sensor system may be compatible with the AFE-based EEG sensor system of the present disclosure. As such, the sensor network can incorporate SSNs for sensing non-physiological activity, such as location (e.g., GPS), noise, environmental conditions (e.g., air temperature, etc.), and so forth.

As a result, the sensor network disclosed herein is fully reconfigurable, modular, and "plug-and-play" compatible. With respect to traditional approaches, clinicians or neurologists are constrained by the lack of available hardware configuration choices with limited compatibility at the time of deployment. Further, each type of neurological or physiological monitoring system usually requires a separate device for sensing and collecting sensor data. However, by eliminating the DRL circuitry, any type of neurological and physiological data can be monitored by simply attaching the corresponding sensor node to the sensor network at the time of deployment. These additional sensor nodes (e.g., one or more other sensor nodes) can be easily added to or removed from the sensor network in LEGO® like fashion. Conversely, the conventional DRL-based systems cannot easily accommodate new sensors, as they are only partially reconfigurable, at best. Notably, such ease of deployment is critical for patients with disorders and vulnerabilities such as epilepsy and Alzheimer's disease, where immediate and flexible deployment of treatment is necessary.

Moreover, the presently disclosed AFE-based EEG sensor system allows for a modular hardware design. To this point, instead of a customized hardware design for each data collection device—as is utilized in the conventional DRL-based EEG sensor system (e.g., at the data collection-level 420)—the AFE-based EEG sensor system utilizes multiple independent and interacting nodes. This promotes modular hardware design for embedded systems, allowing hardware of each node to be upgraded or redesigned without complete redesign of the whole system.

Like the EEG sensor nodes (e.g., FP1, FP2, AF3, AF4, CZ, etc.), the one or more other sensor nodes (e.g., Limb I, Limb II, "other sensors," etc.) may be in communication with the CCN and may transmit information relating to signals detected by the other sensors to the CCN. Moreover, the other sensor nodes may be in communication with the EEG sensor nodes, such that the various sensor nodes at the sensor-level 410 may transmit data among them (e.g., via a bus, as shown in FIG. 4). As such, data processing being performed by a sensor node may be affected by data received from another sensor node. As an example, brain activity detected by an EEG sensor may be analyzed by the EEG sensor node in view of the ambient air temperature sensed by an air temperature sensor connected within the sensor network, whereby the air temperature sensor can send information relating to the ambient air temperature to the EEG sensor node, and vice versa. This way, increasingly complex, descriptive, and useful computations may be performed at the sensor-level 410. Of course, the same type of computations may also be performed at the data collection-level 420 by the CCN.

The reconfigurable sensor network architecture may be realized using an inter-integrated circuit (I2C) topology, for example. The various sensor nodes at sensor-level 410 may be connected within the sensor network in a wired or wireless fashion, in any combination. For instance, a first group of SSNs may use a wired connection to the CCN at the data collection-level 420, while a second group of SSNs may be wirelessly connected to the same CCN, e.g., via a wireless bridge node (WBN) that provides wireless extension of the sensor network to wireless SSNs. This can provide extension to incorporate any types of heterogeneous body-worn sensor nodes, either wired or wireless, within the sensor system disclosed herein.

Figure 5:
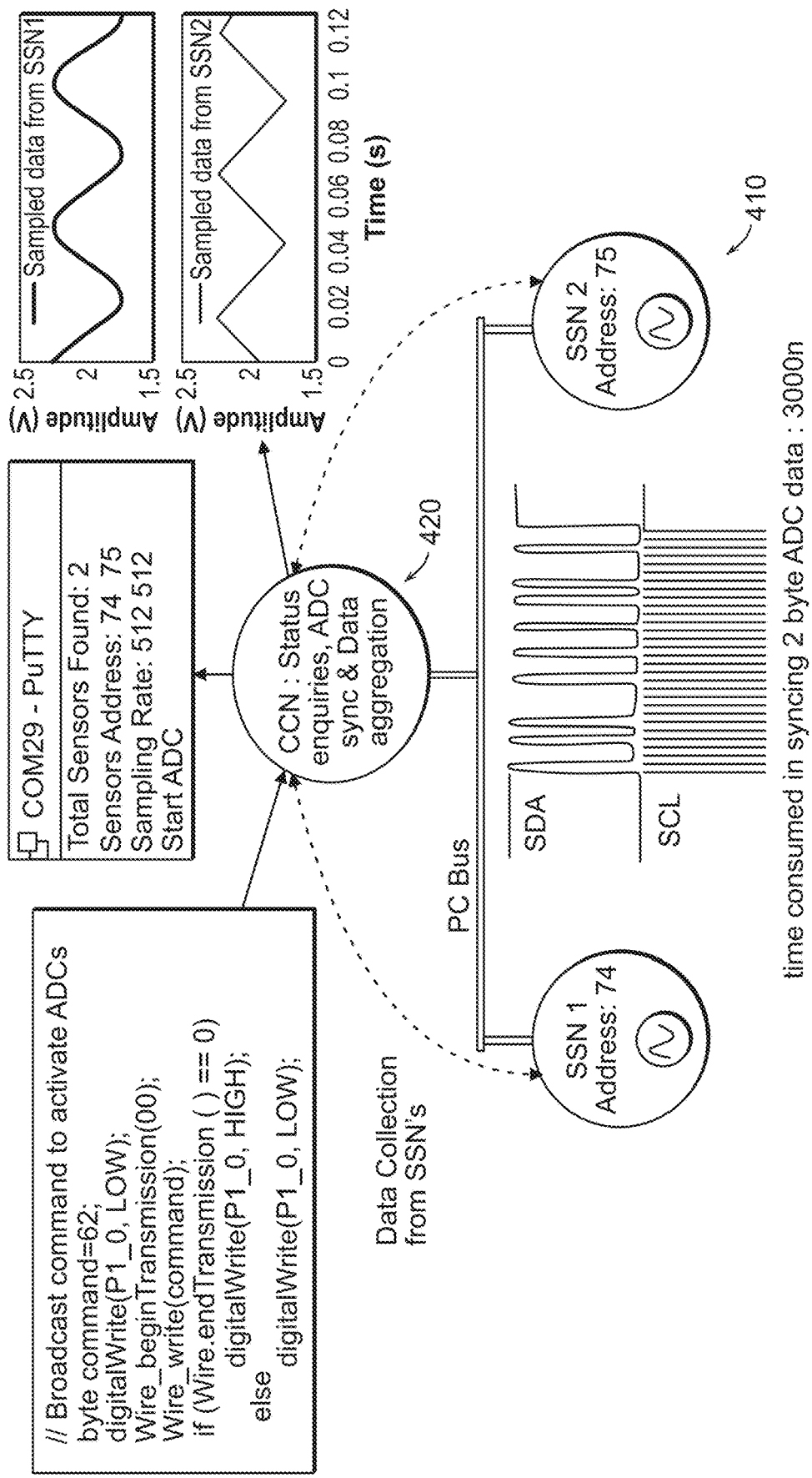
FIG. 5 illustrates an example demonstration for sensor-level modularization in a fully reconfigurable bus architecture according to embodiments of the present disclosure.

FIG. 5 illustrates an example demonstration for sensor-level modularization in a fully reconfigurable bus architecture according to embodiments of the present disclosure. As shown in FIG. 5, two sensors (e.g., "SSN 1" and "SSN 2") at the sensor-level 410, located at distinct addresses, may be communicably connected to one another and to a CCN at the data collection-level 420 via an I2C bus. Signal information, which may include raw signal data and/or processed signal data, may be transmitted from the sensors SSN 1 and SSN 2 to the CCN via the bus. Meanwhile, information (e.g., control commands, signal information, etc.) may be transmitted from the CCN to either or both of the sensors SSN 1 and SSN 2 via the bus.

Upon receiving signal information, the CCN at data collection-level 420 may initiate an analog-to-digital conversion (ADC) of the analog signal obtained by the AFE-based sensors at the SSNs. That is, the analog signal data may be converted to a digital value that represents the signal's amplitude. The CCN may control the ADC process. For example, the CCN may determine the conversion sampling rate, which affects the bandwidth (i.e., the range of measurable frequencies) of the ADC process. Also, the CCN may control the ADC process such that the conversions are performed at a particular periodic rate (e.g., the input signal is "sampled").

Figure 6:
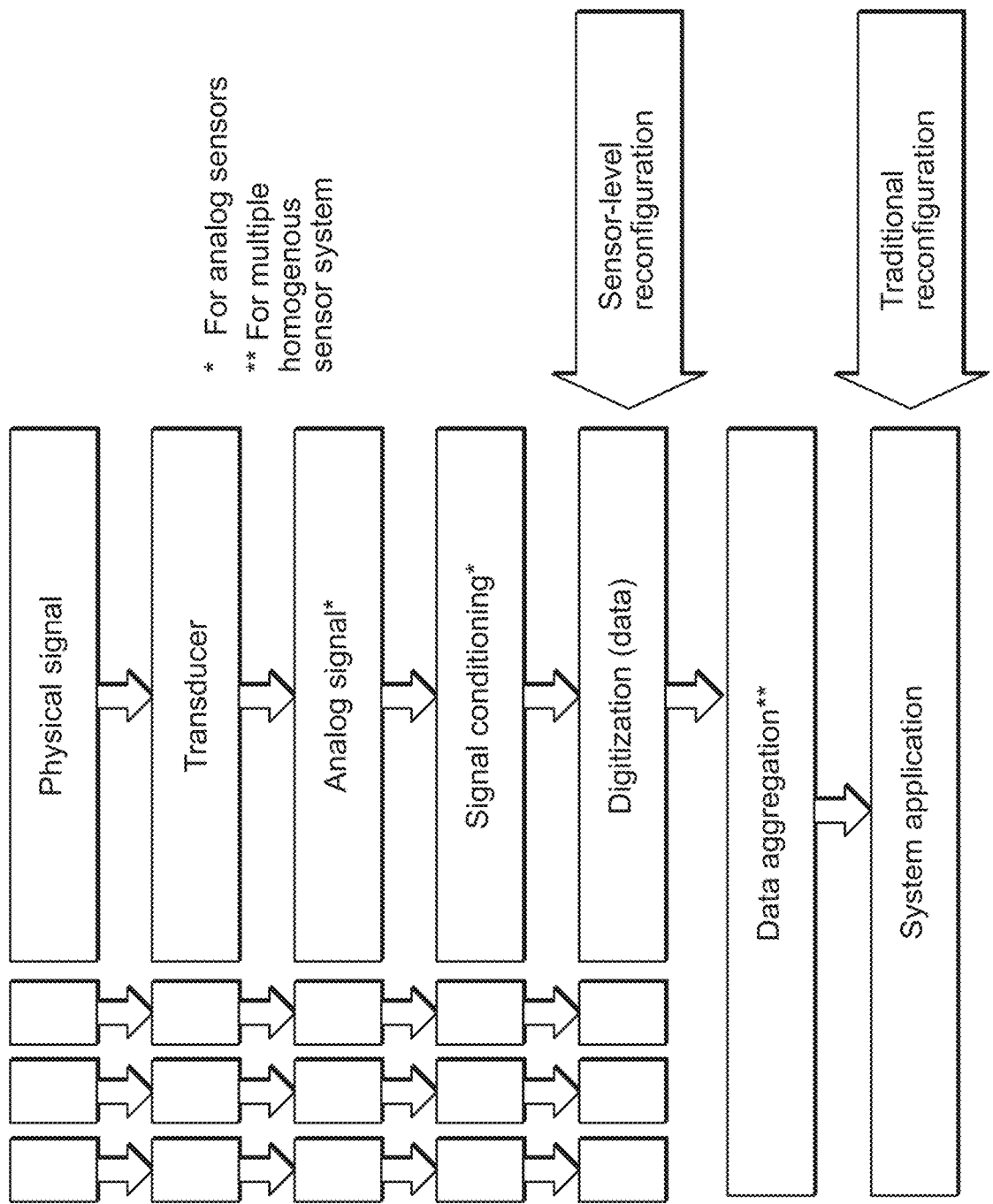
FIG. 6 illustrates an example diagrammatic representation of the distinction between sensor-level reconfiguration according to embodiments of the present disclosure in contrast to conventional system-level reconfiguration for an EEG system with multiple channels.

FIG. 6 illustrates an example diagrammatic representation of the distinction between the presently disclosed sensor-level reconfiguration in contrast to traditional system-level reconfiguration for an EEG system with multiple channels. The disclosed system is able to reconfigure up to sensor-level where the digitized data becomes available. The presently disclosed system can, as well, allow reconfiguration at higher levels, including the data collection-level or system-level. In contrast, traditional systems are usually reconfigured at the system-level only.

Figure 7:
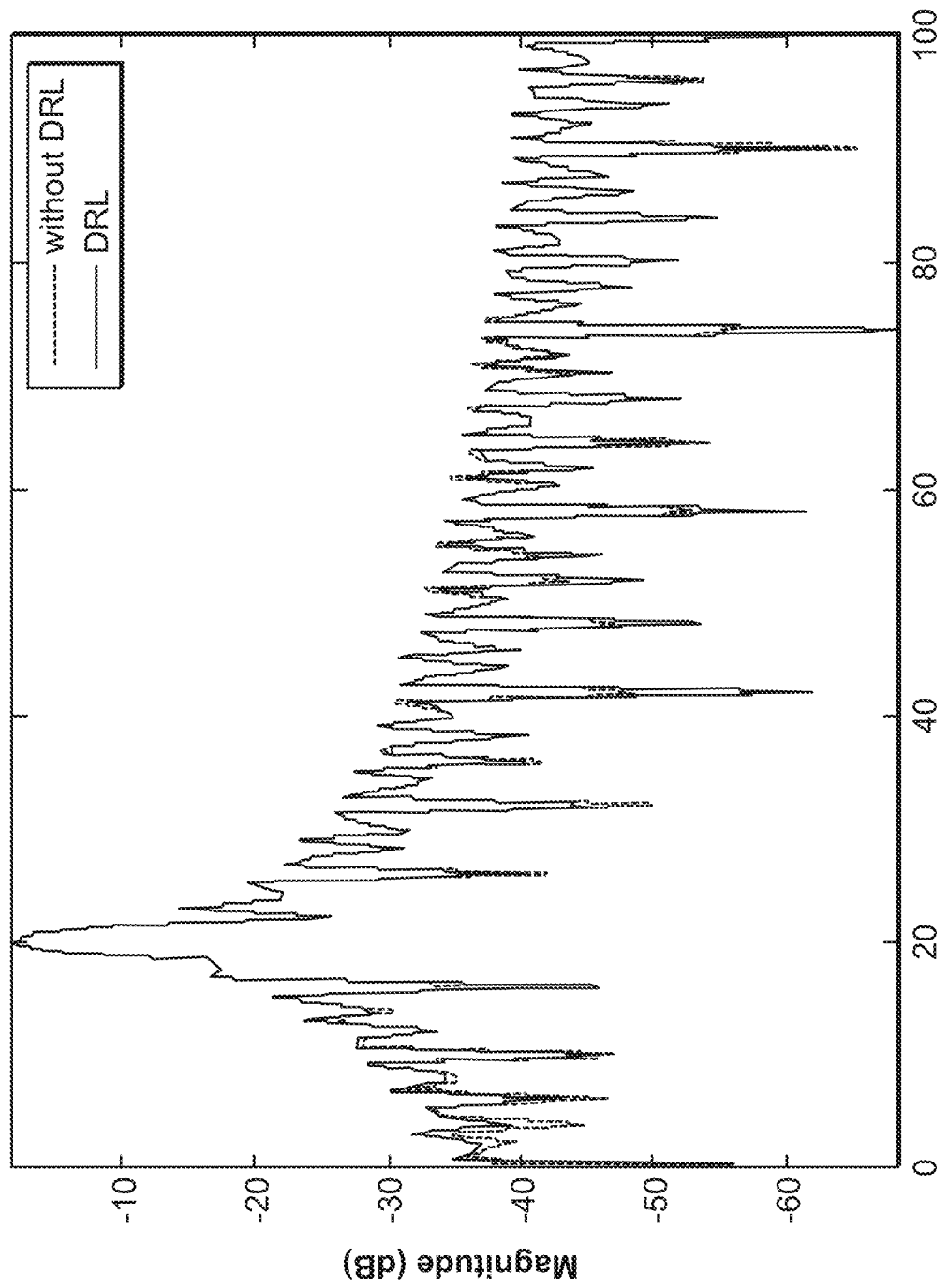
FIGS. 7-9 illustrate test results comparing output signals obtained using the presently disclosed EEG system without DRL circuitry and output signals obtained using traditional EEG systems with DRL circuitry.
Figure 8:
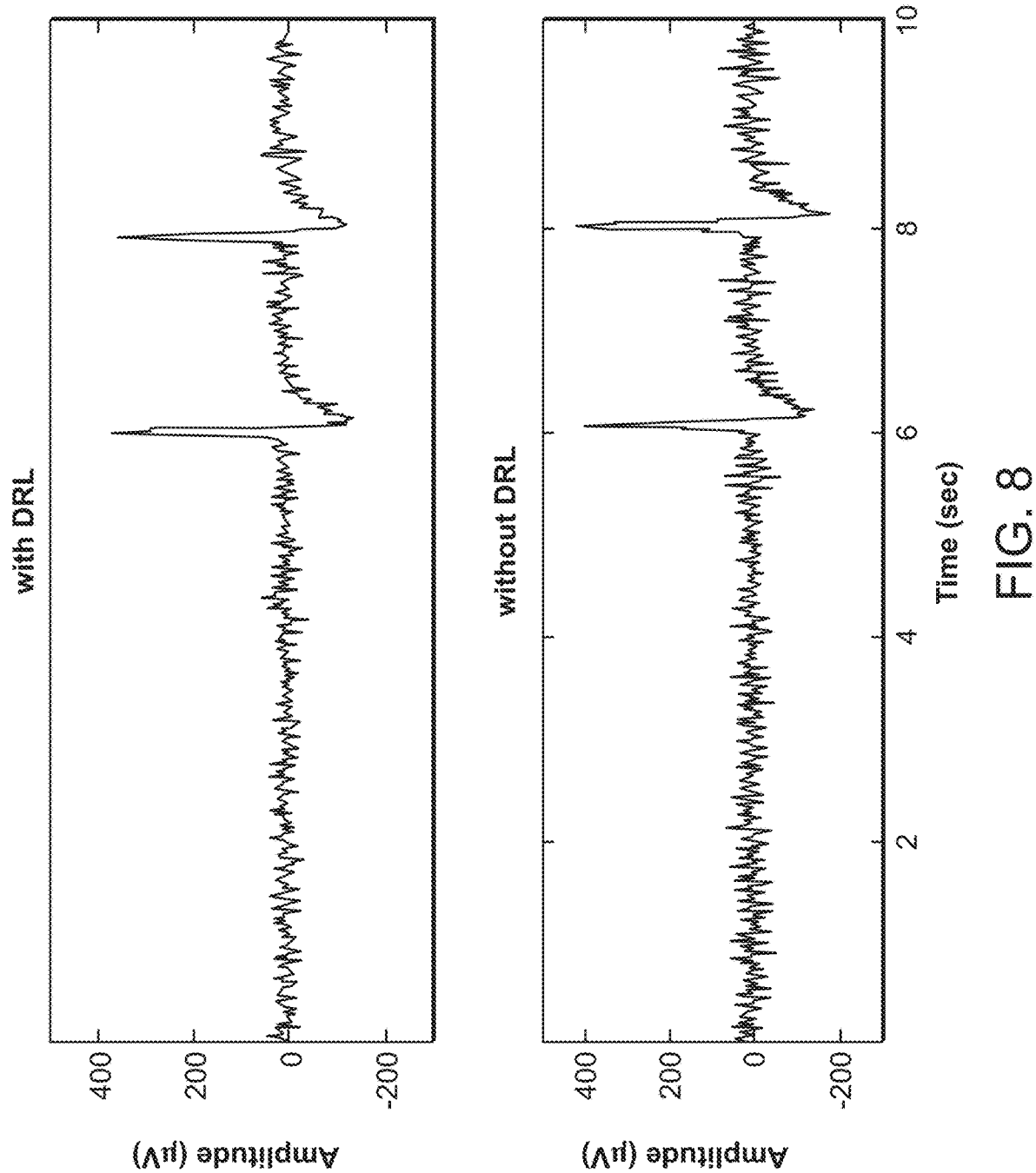
Figure 9:
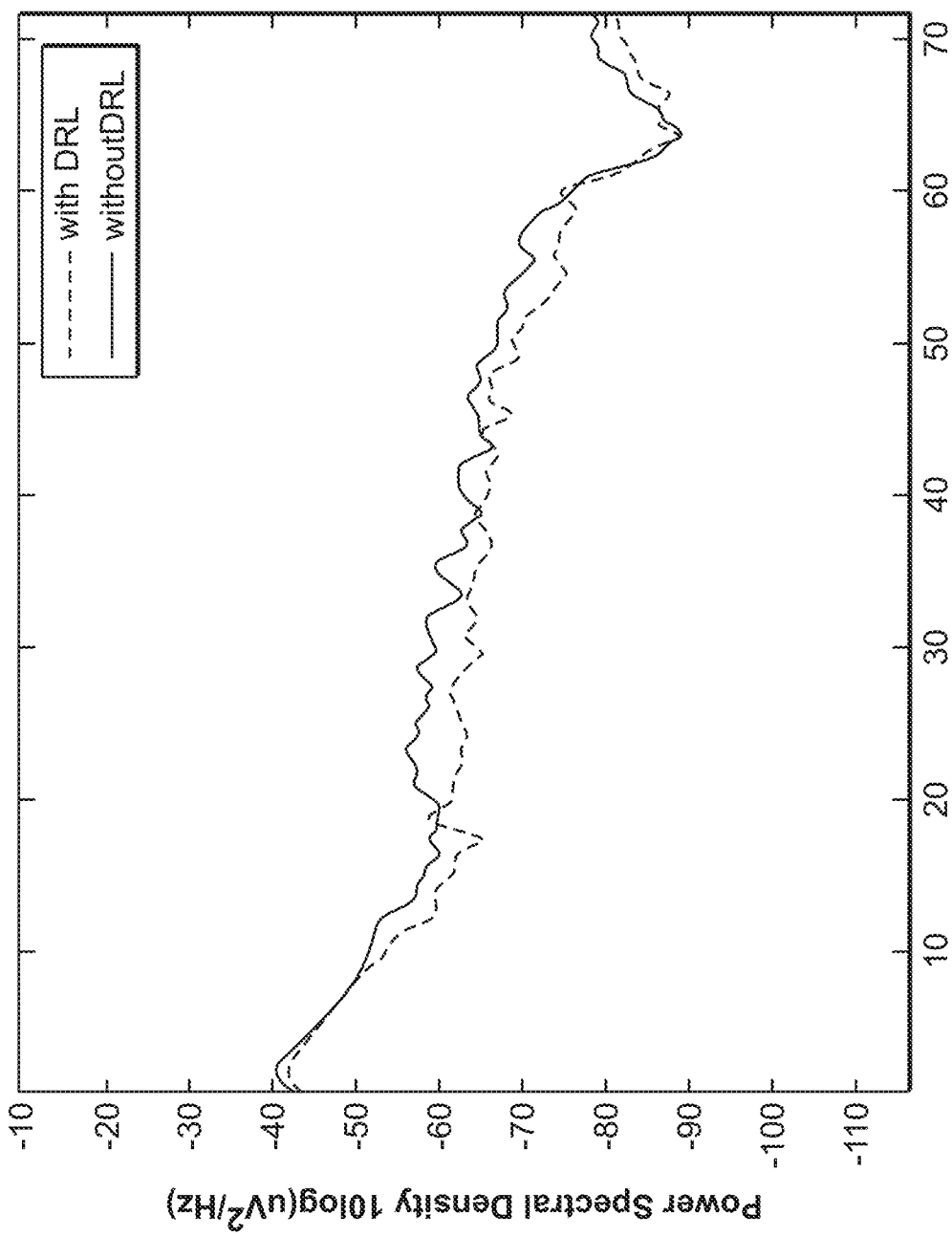

Along these lines, FIGS. 7-9 illustrate test results comparing output signals obtained using the presently disclosed EEG system without DRL circuitry and output signals obtained using traditional EEG systems with DRL circuitry. FIG. 7 depicts a Fast Fourier Transform (FFT) of an output signal obtained with the Device Under Test (DUT) for the input sinusoidal signal, $V_{in}$=4 m$V_{(p-p)}$ at 20 Hz in EEG systems with and without a DRL circuit, respectively. The plot shown in FIG. 7 indicates that the signals obtained with and without DRL are very similar to each other in amplitude over the spectrum, even at 60 Hz frequency where the utility line noise is high. FIG. 8 depicts EEG signals recorded from one subject at the FP2 channel location when the DUT is connected with and without a DRL circuit, respectively. EEG signals recorded from the DUT are shown in FIG. 8 using the Agilent oscilloscope. Eye blinks can be seen conspicuously in the two signals (i.e., at top and bottom), which show almost identical recorded traces. FIG. 9 depicts a power spectral density (PSD) plot of EEG signals from the FP2 location when recorded with and without using a DRL circuit, respectively. In FIG. 9, the PSD of the recorded data is computed using MATLAB with a Hamming window of length 200 over FFT length of 1024 with 50% window overlap. FIG. 9 represents the one-sided PSD for the recorded data. From the PSD plot at 60 Hz, it can be realized that there is merely a difference of 1 dB with and without DRL circuit, suggesting that the elimination of the DRL circuit, as described herein, has an insignificant impact on performance.

The techniques described herein, therefore, provide for a fully customizable and easily deployable LEGO® like, body-worn EEG sensor system for multimodal neuro-physiological monitoring in a naturalistic environment. In particular, sensor-level modularization of EEG (and ECG) is achieved through elimination of DRL circuitry and by subsequently incorporating any body-worn signal monitoring nodes (wired or wireless) within the sensor network. As a result, the presently disclosed AFE-based sensor system described herein can greatly enhance capabilities of neurological and physiological data collection, as well as achieving improvements with respect to ease of deployment, modular hardware design, and distributed intelligence at the sensor-level.

As will be appreciated, the above examples are intended only for the understanding of certain aspects of the techniques herein and are not limiting in nature. For example, the techniques herein may be adapted for use with any form of EEG sensor, as well as ECG/EKG sensors. That is, though EEG systems are primarily referred to herein, for the purposes of the present disclosure, an "EEG system" or "EEG sensor system" also incorporates ECG/EKG systems. In addition, while the techniques disclosed herein are described primarily with respect to a biosensor, it is to be appreciated that the techniques herein may be adapted for use with any other form of remote sensor in addition to those intended to be used with a biological subject (e.g., by measuring a non-biological system).

The foregoing description has been directed to specific embodiments. It will be apparent, however, that other variations and modifications may be made to the described embodiments, with the attainment of some or all of their advantages. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A system comprising:
one or more electroencephalography (EEG) sensor nodes in a reconfigurable sensor network configured to detect electrical signals indicating activity of a brain of a subject and to transmit signal information relating to the detected electrical signals, each EEG sensor node embodying an analog front end (AFE) circuit;
a centralized command control node (CCN) in the sensor network in communication with the one or more EEG sensor nodes and configured to receive the transmitted signal information from the one or more EEG sensor nodes and to perform a processing technique on the received information resulting in processed signal data; and
one or more other sensor nodes, other than EEG sensor nodes, connected in the sensor network, in communication with the CCN, and configured to detect other signals and to transmit information relating to the detected other signals to the CCN;
wherein the one or more EEG sensor nodes are configured to detect the electrical signals without a driven right leg (DRL) circuit in the reconfigurable sensor network;

further wherein the one or more EEG sensor nodes and the one or more other sensor nodes in the sensor network are configured to transmit data among themselves, and to perform data processing on data received from another sensor node; and further wherein the reconfigurable sensor network is adapted to allow plug-and-play reconfiguration of the one or more EEG sensor nodes during deployment, wherein said sensor nodes comprise plug-and-play modules.

2. The system of claim 1, wherein the one or more EEG sensor nodes are in communication with the one or more other sensor nodes.

3. The system of claim 1, wherein the one or more EEG sensor nodes and the one or more other sensor nodes are each configured to be worn by the subject.

4. The system of claim 1, wherein the other signals are associated with physiological data of the subject.

5. The system of claim 1, wherein the other signals are associated with nonphysiological data of the subject.

6. The system of claim 1, wherein the CCN is wirelessly in communication with the one or more EEG sensor nodes, the one or more other sensor nodes, or both.

7. The system of claim 1, wherein the one or more EEG sensor nodes are further configured to locally perform a processing technique on the detected electrical signals resulting in processed signal data and to transmit the processed signal data to the CCN.

8. The system of claim 1, wherein the AFE circuit includes, in order, a first amplifier, a plurality of filters, and a second amplifier.

9. The system of claim 1, wherein the sensor network is configured according to an inter-integrated circuit (I2C) topology.

10. The system of claim 1, wherein the CCN is further configured to control an aspect of the sensor network and to control an aspect of the one or more EEG sensor nodes.

11. The system of claim 1, wherein the CCN is further configured to dynamically control the one or more EEG sensor nodes so as to adapt to a changing condition associated with the subject.

12. The system of claim 1, wherein a wireless bridge node (WBN) provides wireless extension of the sensor network to one or more wireless sensor nodes.

13. A method comprising:
detecting, by one or more electroencephalography (EEG) sensor nodes in a reconfigurable sensor network, electrical signals indicating activity of a brain of a subject, each EEG sensor node embodying an analog front end (AFE) circuit;

transmitting, from the one or more EEG sensor nodes, signal information relating to the detected electrical signals to a centralized command control node (CCN) in the sensor network configured to perform a processing technique on the transmitted information;

detecting, by one or more other sensor nodes, other than EEG sensor nodes, connected to the sensor network, other non-EEG signals; and transmitting, from the one or more other sensor nodes, other non-EEG signal information relating to the detected non-EEG signals to the CCN;

wherein the one or more EEG sensor nodes detect the electrical signals without a driven right leg (DRL) circuit in the reconfigurable sensor network;

further wherein the one or more EEG sensor nodes and the one or more other sensor nodes in the sensor network are configured to transmit data among themselves, and to perform data processing on data received from another sensor node; and further wherein the reconfigurable sensor network is adapted to allow plug-and-play reconfiguration of the one or more EEG sensor nodes during deployment, wherein said sensor nodes comprise plug-and-play modules.

14. The method of claim 13, further comprising:
locally performing, by the one or more EEG sensor nodes, a processing technique on the detected electrical signals resulting in processed signal data; and transmitting, from the one or more EEG sensor nodes, the processed signal data to the CCN.

* * * * *